United States Patent
Larson

(10) Patent No.: US 6,423,742 B1
(45) Date of Patent: Jul. 23, 2002

(54) COMPOSITIONS FOR REDUCING VASCULAR PLAQUE FORMATION AND METHODS OF USING SAME

(76) Inventor: Drake Larson, 78360 Via Sevilla, La Quinta, CA (US) 92253

( * ) Notice: Subject to any disclaimer, the term of this patent is extended or adjusted under 35 U.S.C. 154(b) by 23 days.

(21) Appl. No.: 09/655,400

(22) Filed: Sep. 5, 2000

Related U.S. Application Data

(60) Provisional application No. 60/152,172, filed on Sep. 2, 1999.

(51) Int. Cl.$^7$ .......................... A61K 31/35; A61K 31/19
(52) U.S. Cl. ........................ 514/453; 514/568; 514/824; 514/529; 514/729
(58) Field of Search .............................. 514/453, 568, 514/824, 529, 729

(56) References Cited

U.S. PATENT DOCUMENTS

| | | | |
|---|---|---|---|
| 3,882,248 A | | 5/1975 | Igimi et al. |
| 4,226,788 A | | 10/1980 | DeLuca et al. |
| 4,707,360 A | | 11/1987 | Brasey |
| 5,470,877 A | * | 11/1995 | Gould et al. .............. 514/529 |
| 5,648,377 A | | 7/1997 | Bombardelli et al. |
| 5,855,944 A | | 1/1999 | Koschinski et al. |
| 6,133,311 A | * | 10/2000 | Bok et al. .................. 514/453 |

FOREIGN PATENT DOCUMENTS

| | | | |
|---|---|---|---|
| DE | 19915102 | * | 10/2000 |
| JP | 07223941 | * | 8/1995 |

OTHER PUBLICATIONS

Tarasova, "Polyphenols as potential antisclerotic agents." Abstract: Fenol'nye Soedin. Ikh Biol. Funkts., Mater. Vses. Simp., 1$^s$ (1968), vol. date 1966, 377–83.*
Crowell et al., Cancer Chemother. Pharmacol (1994), vol. 35(1): 35–7 (Abstract Only).
De Feyter et al., Eur. Heart. J. (1995), 16 Suppl I: 26–30. (Abstract Only).
Fulton et al., J. Surg. Res (1997), vol. 69(1): 128–34. (Abstract Only).
Ikechukwu et al., J. Chromatogr. B. Biomed. Sci. Appl. (1997), vol. 688 (2): 354–8 (Abstract Only).
Phillips et al., Drug Metab. Dispos. (1995), vol. 23(7): 676–680 (Abstract Only).
Schaefer et al., J. Investig. Med. (1997), vol. 45(9): 536–41. (Abstract Only).
Thompson, GR, Cardiology (1990), vol. 77 Suppl 4:66–9 (Abstract Only).
Uedo et al., Cancer Letters (1999), vol. 137:131–136. (Abstract Only).
Vigushin et al., Cancer Chemother. Pharmacol. (1998), vol. 42(2): 111–7. (Abstract Only).
Yamakoshi et al., Atherosclerosis (1999), vol. 142(1): 139–49. (Abstract Only).
Zhang, et al., J Gas Chromatogr. B. Biomed. Sci. Appl. (1999), vol. 728(1): 85–95.

* cited by examiner

Primary Examiner—Ralph Gitomer
Assistant Examiner—Devesh Khare
(74) Attorney, Agent, or Firm—Chalin A. Smith; Smith Patent Consulting

(57) ABSTRACT

Described herein are novel, therapeutic pharmaceutical and nutraceutical compositions useful for treating stenotic vascular diseases and disorders, such as atherosclerosis and coronary artery disease, and reducing formation of plaque on vascular walls and methods of using same. More particularly, the present invention relates to dietary supplements comprised of gallic acid, or a derivative thereof, in combination with limonene, or a derivative thereof, formulated so as to effectively reduce plaque formation, reversing plaque deposition and degenerative changes in the arterial walls, and/or removal of existing plaques from the vascular walls of animals, preferably humans. The dietary supplements may be formulated "neat" (e.g., without additives) or with additives such as pharmaceutical carriers, diluents, buffers, adjuvants, excipients, surfactants, and stabilizers. Additionally, the invention relates to a non-invasive diagnostic test and method of using same to assess and monitor a patients potential or predisposition for a heart attack.

24 Claims, No Drawings

COMPOSITIONS FOR REDUCING VASCULAR PLAQUE FORMATION AND METHODS OF USING SAME

CROSS-REFERENCE TO RELATED APPLICATIONS

This application claims the benefit of U.S. Provisional Application Ser. No. 60/152,172, filed Sep. 2, 1999.

TECHNICAL FIELD AND INDUSTRIAL APPLICABILITY OF THE INVENTION

The present invention is related to novel, therapeutic pharmaceutical and nutraceutical compositions useful in treating stenotic vascular diseases and disorders, such as atherosclerosis (also known as arteriosclerosis) and coronary heart disease (also known as coronary artery disease and ischemic heart disease). More particularly, the present invention relates to dietary supplements comprised of gallic acid, or a derivative thereof, and limonene, or a derivative thereof, formulated with or without additives, excipients, and/or stabilizers. The invention further relates to the use of such therapeutic compositions to reduce vascular plaque formation, reverse plaque deposition and degenerative changes in the arterial walls, and/or remove or stabilize existing plaques from the vascular walls. Additionally, the invention relates to a non-invasive diagnostic test and method of using same to monitor a patient's potential for a heart attack.

BACKGROUND OF THE INVENTION

Stenotic vascular diseases and disorders constitute the primary cause of death in industrialized societies. Exemplary stenotic vascular diseases include coronary heart disease (CHD) and peripheral vascular disease (PVD). These diseases generally result from accumulation of "plaque", often deposited slowly over time on vascular walls of arteries. "Plaque" is a generic term describing a heterogeneous sludge of hardened fat, cholesterol, white blood cells, calcium, decaying tissue, and other cellular "garbage." Over time, wear and tear inside the blood vessel walls create rough spots on which plaque can "catch" and build up, eventually blocking blood flow through those vessels. This condition is called atherosclerosis, or "hardening of the arteries."

Atherosclerosis, the underlying condition implicated in most myocardial infarctions and strokes, is a complex pathologic process involving the inner layer (intima) of the arteries. Theories relating to the etiology of atherosclerosis are many and vary from genetic and ecologic factors to levels of lipids in the bloodstream to injury of the arterial wall. While the normal intima serves as a barrier to the influx of serum cholesterol, during atherogenesis the arterial intima breaks down, permitting the entry of blood constituents. With this increase in permeability there is an uptake of particles normally excluded form the vessel wall.

In the early stages, the atherosclerotic lesion is comprised primarily of fatty substances, such as lipid-laden macrophages (white blood cells) and lipid-laden smooth muscle cells. Cholesterol crystals, necrotic debris and calcium deposits are also found in atherosclerotic lesions. As the disease progresses, a dense fibrous cap of smooth muscle and connective tissues develops over the lipid-rich plaque lesion. As the deposition of debris progresses, the lumen of the artery is narrowed and/or obstructed, thereby resulting in diminished or occluded blood flow.

These occluding atherosclerotic lesions ultimately result in ischemia and/or infarction of the affected organ or anatomical part (e.g., the brain, heart, intestine or extremities). In other cases, the plaque tears or ruptures, triggering the formation of a blood clot that can block the artery and lead to a heart attack. Such an event is sometimes called a coronary thrombosis or coronary occlusion. Alternatively, the plaque may cause the arterial wall to become so weakened that soft and/or brittle areas can become segmentally dilated (aneurysmal) and rupture or crack leading to hemorrhage. In any of these events, if the blood supply is cut off severely or for a long time, the result can be significant, often times irreversible, loss of function and cellular substance and may require requiring emergency medical and/or surgical procedures as well. Disability or death can result, depending on how much the tissue (such as the heart muscle) is damaged.

While the basic definitive cause (or causes) of atherosclerosis are not fully known or understood, most therapies are directed to means and methods for affecting deposition of plaque and/or improving arterial flow and function. Examples of the latter include the administration of beta blockers to function as governors on the heart, and aspirin therapy to thin and prevent clotting of the blood. While these may provide some benefit, more preferred therapies are directed at the former, i.e., reducing or preventing vascular plaque formation and removing or dissolving existing plaques.

In light of the empiric clinical observations of many investigators and medical practitioners, it has been hypothesized that plaque formation is related to the plasma cholesterol and lipid levels. Consequently, the most favored regimens for treating atherosclerosis consists of medication, dietary management, behavior modification and exercise aimed at controlling and reducing the plasma cholesterol levels. For examples of specific therapies, see de Feyter P J et al., *Eur Heart J* (1995) 16 Suppl. 1:26–30 and Thompson G R, *Cardiology* (1990) 77 Suppl. 4:66–69.

Exemplary cholesterol-lowering agents include Atromid-S™ (clofibrate), Choloxin™ (dextrothyroxine sodium), Colestid™ (colestipol hydrochloride), Lopid™ (gemfibrozil), Lorelco™ (probucol), Nicolar™ (niacin/nicotinic acid) and Questran™ (cholestyramine resin).

Flavonoids and polyphenols have also been described in the literature as "cardiovascular protecting agents" (see U.S. Pat. No. 5,648,377; U.S. Pat. No. 4,707,360; Bohr D., *J Pharmacol. Exp. Ther.* (1949) 97: 243; Haeger K. Zbl., *Phlebol.* (1967) 6:526; Allen S., *Practioner* (1970) 205:221; Gugler R., *Ces. Arch. Exp. Pathol. Pharm.* (1972) 247:45; Klurfeld, *Exp. Mol. Path.*(1981) 34:62; Lisunetz H., *Polyphenols*, (1990) 764; Frankel E., *Lancet* (1993) 341:454; Kontek A., *Polyphenols* (1995) 94; Folts J., Circul (1995) 91: 1182; Yamakoshi et al. (1999) *Atherosclerosis* 142(1):139–49).

However, these drugs, and the treatments in general are typically directed only at the cause, and not the result of, atherosclerosis, and have not been shown to be effective in reversing the plaque deposition and degenerative changes in the arterial walls. These pharmacologic agents have many other shortcomings such as, for example, adverse side effects (hypertension, cardiac arrhythmias, gastrointestinal disturbances, headache, hypersensitivity, etc.), substantial contraindications (heart, liver or kidney disease, pregnancy, etc.), requirement for lifelong conscientious administration, difficulty in maintaining consistent patient compliance, variable reliability and high cost.

Unfortunately, drug and diet therapies are frequently insufficient to control atherosclerosis. Once the disease has progressed to the stage of significant persistent symptoms and compromised function, more invasive procedures, such as angioplasty, atherectomy, arterial stenting and grafting, and by-pass surgery, are often required. Clearly, surgery is not the solution to the pathologic process since it has no arresting or reversing effect on the progress of the disease and only temporarily overcomes the most critically affected artery (or arteries) by bypassing them, if possible. Surgery is only effective in isolated symptomatic lesions and cannot affect the multitude of atherosclerotic lesions throughout the body. In fact, it is often only a temporary solution as lesion recurrence and restenosis occur in most cases. Moreover, there is a significant risk of morbidity and mortality associated with surgery which many patients are reluctant to accept. Indeed, the disease may continue to progress even as the operation is being performed, and the autogenous veins or arteries used to bypass the disease impaired arteries undergo atherosclerotic changes postoperatively generally at a faster rate than the original, affected arteries.

Thus, there is clearly a need for alternate compositions and methods for treating atherosclerosis and its underlying cause, i.e., vascular plaque formation. The present invention attempts to address the drawbacks and disadvantages of current therapies by providing pharmaceutical and nutritional compositions for simply, safely, and non-invasively inhibiting plaque formation, removing existing plaques and/or reversing plaque deposition and degenerative changes in the arterial walls.

The present invention further provides a diagnostic test and associated method for assessing and monitoring a patient's potential or predisposition for heart attack. Current techniques for diagnosing and monitoring atherosclerosis and vascular plaque progression are generally invasive and include, for example, internal Doppler ultrasound, atherectomic biopsies, and catheterized X-ray angiography (see Schaeffer et al., *J Investig Med* (1997) 45(9):536–41). Though less invasive monitoring techniques, such as external magnetic resonance imaging (MRI) and external Doppler ultrasound, are gaining favor, there continues to be a need for diagnostics that provide both quantitative and qualitative results that, in turn, suggest proper counteractive measures. The minimally invasive diagnostic test and method of the present invention addresses this need.

SUMMARY OF THE INVENTION

Accordingly, one object of the invention is to provide a method for treating stenotic vascular diseases and disorders, such as atherosclerosis and coronary artery disease, comprising administering to a patient in need thereof a therapeutically effective amount of limonene, or a derivative thereof, either alone or in combination with gallic acid, or a derivative thereof. In the context of the present invention, "treatment" involves one or more of the following: (a) the reduction of plaque formation of the vascular walls; (b) the reversal of plaque deposition and degenerative changes in the arterial walls; and (c) the removal or stabilization of existing vascular plaques; or (d) the enhancement of cholesterol solubility in plasma.

A further object of the invention is to provide a therapeutic composition effective for the treatment of atherosclerosis, or a cause or symptom thereof, comprising an effective amount of gallic acid, or a derivative thereof, and an effective amount of limonene, or a derivative thereof. In one preferred embodiment, the therapeutic composition comprises about 35 wt. % to about 70 wt. % gallic acid, or a derivative thereof, and about 5 wt. % to about 55 wt. % limonene, or a derivative thereof.

In another embodiment, the therapeutic composition includes one or more stabilizing agents, such as salts, tannic acid, ascorbic acid lecithin, and tocopherols. In one preferred embodiment, the stabilizing agent comprises about 10 wt. % to about 60 wt. % of the entire composition.

The therapeutic compositions and methods of the present invention preferably provide for the inhibition of the formation (e.g., progression) of atherosclerotic plaques and/or the removal of existing plaque from vascular walls of animals, particularly humans.

A further object of the present invention is to provide therapeutic compositions and method that further aid in stabilizing plaques. By "plaque stabilization", it is meant the inhibition of plaque passing through a phase in which the lipid core has grown and the fibrous cap is very thin and vulnerable to rupture due to an increase in the density of macrophages.

A further object of the present invention is to provide therapeutic compositions and method that are particularly effective in encouraging or increasing cholesterol solubility and also in reversing the arterial plaque deposition and degenerative changes to substantially arrest, alleviate and, to a certain extent, even cure the many and varied problems, conditions and secondary complications associated with atherosclerosis.

Yet another object of the present invention is to provide a diagnostic test and method for diagnosing a patient's potential or predisposition for heart attack comprising the steps of:

(a) administering a composition comprising an effective amount of limonene, or a derivative thereof, to said patient, said amount being effective to solubilize contents of vascular plaques so as to be at least temporarily circulating in the blood;

(b) periodically taking blood samples from said patient;

(c) assaying the chemical composition of said samples to obtain a plasma profile;

(d) comparing said plasma profile with known risk factors; and (e) correlating the information obtained in step (d) to a patient's potential or predisposition for heart attack.

In an alternate embodiment, the diagnostic test and method for diagnosing a patient's potential or predisposition for heart attack comprising the steps of:

(a) taking a biopsy sample from a patient's atherosclerotic plaque;

(b) diluting said sample with an amount limonene;

(c) assaying the chemical composition of said samples to obtain a plasma profile;

(d) comparing said plasma profile with known risk factors; and (e) correlating the information obtained in step (d) to a patient's potential or predisposition for heart attack.

In a further embodiment, the plasma profile information obtained in step (d) above is used to determine an appropriate interventional therapy.

In another further embodiment, the plasma profile information obtained in step (d) above is used to monitor the effectiveness of interventional therapy.

In another further embodiment, the plasma profile information obtained in step (d) above is used to individualize the prescribed interventional therapy, the therapy preferably including the administration of a composition comprising a therapeutically effective amount of gallic acid, or a derivative thereof, and a therapeutically effective amount of limonene, or a derivative thereof.

These and other objects and features of the invention will become more fully apparent when the following detailed description is read in conjunction with the accompanying figures and examples.

DETAILED DESCRIPTION AND PREFERRED EMBODIMENTS OF THE INVENTION

The present invention relates to therapeutic compositions and methods for the treatment of stenotic vascular diseases and disorders, particularly atherosclerosis. Plaque formation on vascular walls of animals, particularly humans, can be reduced by administering a pharmaceutically acceptable combination of gallic acid (or a derivative thereof) and limonene (or a derivative thereof). Antioxidant stabilizing agents may also be added to induce ligand bonds between the gallic acid and limonene or tannins and limonene.

At varying concentrations, the therapeutic compositions of the present invention may be formulated as a pill, capsule, powder, liquid, lotion, suppository, spray, dietary supplement or the like, so as to reduce adhesion of plaque to the vascular walls. The particular formulation will determine the mode of administration and vice versa. Exemplary methods of administering the therapeutic formulations include, but are not limited to, oral ingestion, parenteral introduction, topical application, and vaginal, rectal, and nasal delivery.

Such administration should decrease the formation of plaque on the vascular walls, such as occurs during atherosclerosis. Adhesion of plaque to the vascular walls results from activity of various compounds both aqueous and lipid soluble, cells, and bacteria in the blood. The formulation of the invention minimizes or prevents unhealthy plaque deposits from accumulating on the vascular walls. In addition, the therapeutic compositions can be conveniently formulated in lotions and foodstuffs.

A. Therapeutic Compositions and Active Ingredients Therein

As mentioned above, the therapeutic compositions comprise an effective amount of gallic acid, or a derivative thereof, and an effective amount of limonene, or a derivative thereof. As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the reduction of plaque formation of the vascular walls; (b) the reversal of plaque deposition and degenerative changes in the arterial walls; (c) the removal or stabilization of existing vascular plaques; or (d) the enhancement of cholesterol solubility in plasma. The optimum effective amounts can be readily determined by one of ordinary skill in the art using routine experimentation.

As mentioned above, one of the active ingredients present in the inventive therapeutic compositions is gallic acid or a derivative thereof. Gallic acid, also known as 3,4,5-trihydroxybenzoic acid $[C_6H_2(OH)_3CO_2H]$, is a colorless crystalline organic acid found in gallnuts, sumach, tea leaves, oak bark, and many other plants, both in its free state and as part of the tannin molecule. The molecular structure of gallic acid is shown below:

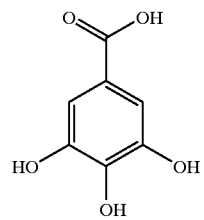

Gallic acid may comprise from about 1 wt. % to about 90 wt. %, preferably from about 15 wt. % to about 85 wt. %, more preferably from about 35 wt. % to about 70 wt. % of the total composition.

Since gallic acid has hydroxyl groups and a carboxylic acid group in the same molecule, two molecules of it can react with one another to form an ester, digallic acid. Gallic acid can be also obtained by the alkaline or acid hydrolysis of tannins. Tannic acid, also known as gallotannic acid, is an astringent vegetable product found in a wide variety of plants. Sources of tannin and tannic acid include the bark of oak, hemlock, chestnut, and mangrove; the leaves of certain sumacs; and plant galls. Tannin is also present in tea, coffee, and walnuts. Tannin varies somewhat in composition, having the approximate empirical formula $C_{76}H_{52}O_{46}$. The molecular structure of tannic acids is shown below:

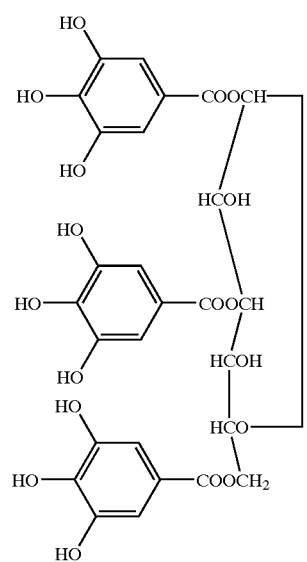

In the context of the present invention, tannins, and particularly tannic acid, are considered to be derivatives of gallic acid.

Another active ingredient present in the inventive therapeutic compositions is limonene or a derivative thereof. Limonene $[C_{10}H_{16};$ CAS #5989-27-5] is monocyclic monoterpene occurring in nature as the main component of citrus peel oil, having a characteristic lemonlike fragrance. The molecular structure of limonene is shown below:

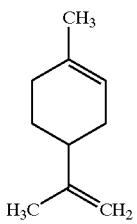

Chemical synonyms of limonene include: 4-isopropenyl-1-methylcyclohexene;
acintene dipentene; cajeputene; cinene; dipanol; dipentene; kautschin; p-mentha-1,8-diene; dl-1,8(9)-p-menthadiene; p-menthane; 1-p-mentha-1,8-diene; nesol; delta-1,8-terpodiene; methyl-4-isopropenyl-1-cyclohexene; and 1-methyl-4-(1-methylethenyl) cyclohexene. Limonene may comprise from about 1 wt. % to about 90 wt. %, preferably from about 5 wt. % to about 65 wt. %, more preferably from about 5 wt. % to about 55 wt. % of the total composition.

Limonene is commonly though of as a solvent, having a KB value of 67. Recent findings suggest that limonene may inhibit the development of gastric cancers through increased apoptosis and decreased DNA synthesis (see Uedo et al., *Cancer Letters* (1999) 137:131–136). Limonene and perillyl alcohol together have been shown to induce apoptosis of human vascular smooth muscle cells (HVSMCs), an early cause of atherosclerosis (see Unlu S et al., *J of Cardiovasc Pharmacol* (February, 2000) 35: 341). Preliminary ex-vitro trials of the present invention suggest that the introduction of limonene to human plasma can increase the rate of solubility of cholesterol by 24% over a one hour period; moreover, these same trials suggest limonene may aid in plasma metabolizing excess cholesterol at a minimum rate of 4% per hour (see Example 10). Likewise, limonene derivatives may enhance the activity of gallic acid derivatives as demonstrated in a non-statistically significant mean improvement in rabbits trials by over 20% (see Example 9).

As used herein, "derivatives" includes, but are not limited to, oxidation products, salts, solvates, multimers, prodrugs, and metabolites of the parent compound of interest (e.g., limonene or gallic acid). Preferred derivatives are those which retain the desirable therapeutic activity of the parent compound. Of particular utility are those derivatives that maintain the beneficial characteristics of the parent compound, have a pleasant flavor, are at least mildly polar, and have a specific gravity close to 1.0 so they can be easily used as fortifiers in liquid beverages.

Exemplary derivatives of gallic acid include, but are not limited to, digallic acid, gallotannic acid, partially and fully oxidized compounds of gallic acid resulting in from multimerization of gallic acid, oxidized gallic acid and/or hydrolyzed gallic acid, gallic acid compounds oxidized further in the presence of glucose and the resulting oxidation products thereof. Exemplary derivatives of limonene include, but are not limited to, perillic acid, perillyl alcohol, hydroperillic acid, cis and trans dihydroperillic acid, ellagic acid, methyl esters of these acids, limonene-1,2-diol, and uroterpenol.

As used herein, "oxidation products" are those compounds resulting from an oxidation reaction. They may be partially or fully oxidized. The term "oxidation" is generally defined as the loss of electrons. Oxidation includes, but is not limited to, those reactions where either a hydrogen is removed or an electronegative element, such as oxygen, nitrogen, or halogen, is added. Any reaction that converts a functional group from a lower oxidation state to a higher one is considered "oxidation". This includes a pathway of polymerizing compounds where the result is the neutralization of oxygen's free radicals via a new compound plus water.

An exemplary oxidation reaction is as follows:

$$R+X+1/2(O_2) \rightarrow (R'-X')+H_2O$$

where R, R', X, X' represent compounds and chemical composition of R=R'+H and X=X'+H. R'-R and R'-X' are considered partially oxidized products, multimers of R and/or X.

As used herein, the term "salts" include, but are not limited to, pharmaceutically acceptable addition salts. The functional groups on the active compounds of the present invention can react with any of a number of inorganic or organic bases, or inorganic and organic acids, to form pharmaceutically acceptable addition salts. The salt form of a parent compound is often preferred because it tends to be more soluble in aqueous or other protonic solvents than are the corresponding free-base forms. Exemplary addition salts include, but are not limited to, chlorides, bromides, iodides, acetates, sulfates, sulfites, phosphates, oxalates, malonates, succinates, fumarates, maleates, benzoates, phthalates, sulfonates, propionates, butyrates, citrates, palmitic, lactates, glycollates, and tartrates.

As used herein, the term "solvates" refers to derivative forms a parent compound comprised of the parent structures in combination with solvents. Exemplary solvents include, but are not limited to, water, isopropanol, ethanol, methanol, DMSO, ethyl acetate, acetic acid, or ethanolamine.

As used herein, the term "multimer" refers to multivalent or multimeric forms of the compounds of interest. A "multimer" may be made by linking multiple copies (two or more) of a compound (or a derivative thereof) to each other. The multimer may include linking units disposed between the compound copies. Suitable linking units are known in the art and can be routinely selected to arrive at the optimum multivalency and spacing. Useful linking moieties include those containing a multiplicity of functional groups that can be reacted with functional groups associated with the parent compound or its derivative. Such functional groups include, but are not limited to, amino, sulfhydryl, hydroxyl, and alkylamino groups. These groups are routinely selected to obtain stable linkages between or among the multiple compound copies.

In the context of the present invention, the term "multimer" should be construed to include "polymers", i.e. large molecules formed by the union of at least five identical monomers, usually containing many more than five monomers, and some may contain hundreds or thousands of monomers in each chain.

Exemplary multimers of gallic acid are depicted below:

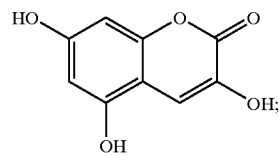

-continued

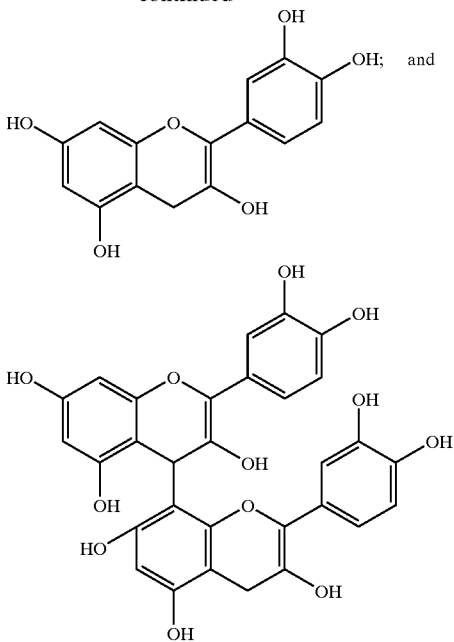

In general, the various compounds described herein may be optionally substituted by one or more functional groups or substituents. Exemplary substituents include halo, guano, amino, nitro, cyano, or acetate groups Examples of substituted gallic acid moities include:

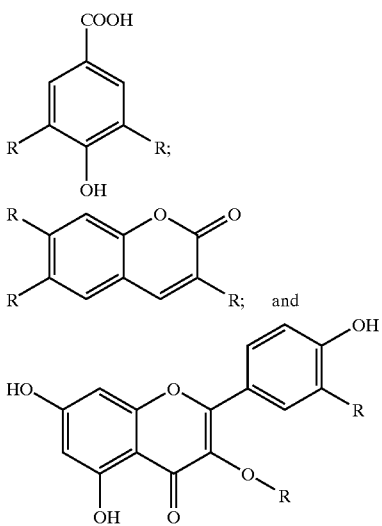

wherein R is halo, guano, amino, nitro, cyano or acetate.

As used herein, the term "prodrug" refers to a precursor of a parent compound that is converted within the body into the parent compound itself or an active derivative form thereof having the prescribed therapeutic activity associated with the compound. Prodrugs are particularly useful when the parent compound is too toxic to administer systemically, is absorbed poorly by the digestive tract, or is broken down by endogenous enzymes before it reaches its target.

As used herein, the term "metabolite" of a parent compound refers to any product produced by the body's metabolism of the parent compound. Both prodrugs and metabolites may be identified using routine techniques known in the art. Exemplary metabolites of limonene have been described in the literature and include, but are not limited to, perillyl alcohol, perillic acid, cis and trans dihydroperillic acid, methyl esters of these acids, limonene-1,2-diol, and uroterpenol (see Ikechukwu et al., *J Chromatogr* (1997) 688(2):354–358; Vigushin et al., *Cancer Chemother Pharmacol* (1998) 42(2):111–7; Zhang-Zhihong et al., *J Chromatogr* (1999) 728(1):85–95; Crowell P et al., *Cancer Chemother Pharmacol* (1994) 35(1):35–37; Fulton GJ et al., *J Surg Res* (1997) 69(1):128–134; and Phillips LR et al., *Drug Metab Disp* (1995) 23(7):676–680).

Some of the compounds described herein may exist in numerous isomeric forms. The present invention is not limited to any single compound depicted or described but extends to include isomers thereof. For example, the compounds are not limited to a single structural isomer but include tautomers thereof. Tautomers are special structural isomers that are readily interconvertible through rapid equilibration. Likewise, the compounds are not limited to a single optical isomer but include enantiomers, diastereomers, and racemate mixtures thereof.

B. Pharmaceutical and Nutraceutical Formulations and Components Thereof

The therapeutic compositions of the present invention may be pharmaceutically or nutraceutically formulated to include beneficial additives such as pharmaceutical carriers, diluents, buffers, adjuvants, excipients, surfactants and stabilizers. The amount of additive present may vary, ranging from about 0.1 wt. % to about 99 wt. %, preferably from about 5 wt. % to about 80 wt. %, more preferably from about 10 wt. % to about 70 wt. % of the total composition.

As atherosclerosis has been postulated to have an infectious or microbial component, the therapeutic compositions of the present invention may further be formulated to include antibiotic or antimicrobial agents. Exemplary antimicrobials include, but are not limited to, salts of bismuth fluoride, chloride, sodium, and zinc. Preferred examples include, but are not limited to, sodium hydroxide, bismuth citrate, bismuth permanganate, bismuth difluoroketone, zinc citrate, zinc permanganate, and zinc difluoroketone.

In a preferred embodiment, the therapeutic composition of the present invention comprises about 15 to about 85 wt. % gallic acid (or a derivative thereof), from about 5 to about 65 wt. % limonene (or a derivative thereof), and, if present, about 20 wt.% to about 60 wt. % additional ingredient (e.g., an antioxidant stabilizer).

Although the therapeutic compositions of the present invention may be formulated "neat" (i.e., without excipients), an especially preferred embodiment comprises gallic acid (or a derivative thereof), limonene (or a derivative thereof), and lecithin, an excipient that acts as both an antioxidant stabilizer and a pH buffer. Lecithin has been shown to particularly cure the gastrointestinal discomfort associated administration of limonene alone (see Example 11).

As used herein, a composition or compound is "pharmaceutically acceptable" if it is suitable for use with humans and/or other animals without undue adverse side effects such as toxicity, irritation, and allergic response.

As used herein, the term "nutraceutical" refers to nutrition and food products, usually from natural sources, having some pharmaceutical benefits.

As used herein, the term "pharmaceutical carrier" refers to pharmaceutically acceptable solvents, suspending agents, liposomes and vehicles for delivering the therapeutic agent (s) to the animal, particularly a human. The carrier may be liquid or solid and varies with the selected administration route. When the carrier serves as a diluent (i.e., a substance that dilutes), it may be a solid, semi-solid, or liquid material acting as a vehicle, excipient, or medium for the active ingredient(s).

As used herein, the terms "buffer" and "buffering agent" refer to additives that adjust and maintain the pH value of a pharmaceutical solution or lyophilized preparation (i.e., the pH on reconstitution) within acceptable ranges. The buffering agents adjust the pH value of the pharmaceutical solution so that the stability of the active agent is maintained. Exemplary buffering agents include, but are not limited to, lecithin, phosphate buffer, Tris buffer and citrate buffer.

As used herein, an "adjuvant" is a substance that, when added to a pharmaceutical composition, either enhances or improves the therapeutic activity of one or more of the active agents contained therein or enhances the overall therapeutic effectiveness of the composition as a whole. A preferred adjuvant for use with the present therapeutic compositions is lecithin, a compound that cures the negative GI side effects of limonene.

As used herein, the term "pharmaceutical excipient" refers to any more or less inert, non-toxic substance added to a pharmaceutical composition in order to confer some benefit thereto, such as improved physical and/or chemical stability or improved handling characteristics (e.g., flowability and consistency). In other embodiments, the excipient merely serves as a bulking agent, reducing the concentration of the therapeutic agent in the pharmaceutical composition. Exemplary pharmaceutical excipients include, but are not limited to, proteins, peptides, amino acids, lipids, polymers, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which may be present singly or in combination.

As used herein, a "surfactant" is an excipient having surface activity/Exemplary surfactants include, but are not limited to, Tween 80, Tween 20, Pluronic F-68, polyethylene glycol, and the like.

Antioxidants, when exposed to air or water at room temperature, tend to be neutralized over time. In plasma, these neutralized "antioxidants" become "oxidants". For example, studies have shown that while fresh polyphenols, such as those found in grapes, can prevent atherosclerosis, those stored at room temperature for 18 months or more tend to enhance the causes of atherosclerosis. Thus, a preferred therapeutic composition will contain the proper stabilizing agent(s).

As used herein, a "stabilizer" is an excipient that improves the stability (e.g., the storage stability) of the pharmaceutical composition, helping to maintain the therapeutic activity of the active agent(s) disposed therein. Exemplary stabilizers include, but are not limited to, amino acids, such as glycine, and sugar alcohols, such as mannitol. The stabilizing agent preferably comprises from about 10 wt. % to about 60% wt. of the total therapeutic composition.

In a preferred embodiment, the stabilizer is an antioxidant. As used herein, the term "antioxidant" refers to synthetic or natural substances that prevent or delay the oxidative deterioration of a compound. Exemplary antioxidants include lecithin, gamma oryzanol; ubiquinone (ubidecarenone) and coenzyme Q; vitamins, such as vitamins A, C (ascorbic acid) and E and beta-carotene; natural components such as camosol, carnosic acid and rosmanol found in rosemary and hawthorn extract, proanthocyanidins such as those found in grapeseed or pine bark extract, and green tea extract.

A preferred antioxidant for use with the therapeutic compositions of the present invention is lecithin, a compound that cures the negative GI side effects of limonene.

Homologs, analogs and derivatives of such antioxidants are also useful. For example, the principle active component of Vitamin E is tocopherol, particularly α-tocopherol; however, any Vitamin E or tocopherol derivative may be employed. Examples of useful Vitamin E derivatives include, but are not limited to, esters, for example, tocopherol acetate, tocopherol linoleate, tocopherol nicotinate, tocopherol sorbate, or tocopherol succinate; polyethylene glycol ethers of tocopherol, such as tocophereth-5, tocophereth-10, tocophereth-12, tocophereth-18 or tocophereth-50 and 6-hydroxychroman homologues, (such as are described in U.S. Pat. Nos. 4,003,919; 4,018,799; 4,026,907 and 3,903,317) particularly 6-hydroxy-2,5,7,8-tetramethylchroman-2-chroman-2-carboxylic acid, commercially available as Trolox-C™ (Cort et al., *JAOCS* 52: 174, 1975) and Troloxyl-amino acids (Taylor et al., *JAOCS*: 622, 1981).

Examples of useful Vitamin C derivatives include, but are not limited to, ascorbyl esters of fatty acids, such as ascorbyl palmitate, ascorbyl dipalmitate, ascorbyl dimethylsilanol palmitate, and ascorbyl stearate; metal or metal phosphate salts, such as magnesium, sodium, or potassium ascorbyl phosphate, or magnesium, sodium or potassium ascorbate.

Ubiquinone is a naturally occurring hydrogen carrier in the respiratory chain(coenzyme Q); structurally, it is a 2,3-dimethoxy-5-methyl-1,4-benzoquinone with a multiprenyl side chain, the number of isoprene units varying depending upon the organism. Exemplary ubiquinone derivatives are described, for example, in WO 8803015.

C. Therapeutic Utilities

As discussed above, the therapeutic compositions of the present invention are useful as pharmaceuticals (e.g., drugs) or nutraceuticals (e.g., dietary supplements) for treating stenotic vascular diseases and disorders, such as atherosclerosis and coronary artery disease, in patients in need thereof.

While not wishing to be bound by theory, it is believed that the therapeutic compositions of the present invention aid in the prevention and encourage the removal of atherosclerotic plaques by keeping lipids and phospholipids in a more liquid state but also aids in unnecessary thrombocytes aggregation and leukocytes vascular adhesion. The varying concentrations of these compounds in the blood and their vasodilating tendencies aid in the natural removal of unwanted deposits on the endothelium layer by simple mechanical variation of the vascular walls via vasodilation and constriction. The changing of the threshold of thrombocyte aggregation also aids in preventing a sudden heart attack.

The therapeutic compositions may also find utility in the treatment of certain cancers, preventing or inhibiting tumor growth, aggregation, and progression.

In the context of the present invention, the term "animal" encompasses both humans and non-humans. The compositions and methods of the present invention are preferably directed to vertebrate animals, more preferably to mammals (including humans).

Likewise, in the context of the present invention, the term "patient" primarily refers to human subjects, although the formulations of the present invention are also useful in the treatment of animals other than humans.

The specific dosage amount of each active agent being administered to obtain therapeutic or inhibitory effects may be determined in a manner known in the art according to the particular circumstances surrounding the case, including, e.g., the specific agent being administered, the route of administration, the condition being treated, and the subject or host being treated. The total daily dose of a therapeutic composition containing gallic acid (or a derivative thereof), limonene (or a derivative thereof) and optionally an additive (e.g., excipient or stabilizer), administered in single or multiple doses, may range from about 10 to 100,000 milligrams per day. The total daily dosage of gallic acid (or a derivative thereof) may range from about 1.5–8.5 to about 15,000–85,000 milligrams per day preferably from about 10 to 20,000 milligrams per day, more preferably from about 100 to 10,000 milligrams per day. The total daily dosage of limonene (or a derivative thereof) may range from about 0.5–6.5 to about 5000–80,000 milligrams per day, preferably from about 500 to 10,000 milligrams per day, more preferably from about 1000 to 10,000 milligrams per day.

The therapeutic compositions of the present invention may be administered by any of a variety of suitable routes, such as orally, parenterally, rectally, topically, transdermally, subcutaneously, intravenously, intramuscularly, and intranasally.

The agents are preferably formulated into compositions suitable for the desired routes before being administered. The therapeutic compositions may be prepared in any of a variety of forms suitable for the desired mode of administration. Exemplary forms include, but are not limited to, tablets, pills, capsules, powders, sprays, lotions, ointments, liquids, elixirs, suspensions, emulsions, solutions, sprays, aerosols, suppositories, and the like.

The particular dosage form should be selected to match the chosen route of administration. For example, if IV injection is the selected administration route, clearly the agents of the invention should be formulated into aqueous solutions, preferably in physiologically compatible buffers such as Hanks's solution, Ringer's solution, or physiological saline buffer.

D. Diagnostic Applications

As discussed above, the present invention relates to a diagnostic test and method for diagnosing a patient's potential or predisposition for heart attack comprising the steps of:

(a) administering a composition comprising an effective amount of limonene, or a derivative thereof, to said patient, said amount being effective to solubilize contents of vascular plaques so as to be at least temporarily circulating in the blood;

(b) periodically taking blood samples from said patient;

(c) assaying the chemical composition of said samples to obtain a plasma profile;

(d) comparing said plasma profile with known risk factors; and (e) correlating the information obtained in step (d) to a patient's potential or predisposition for heart attack.

The minimally invasive diagnostic test and method described above is suitable for monitoring the potential for a heart attack or as a marker of a predisposition to such an event. Limonene can be used alone or together in any combination with one or more of the following compounds: gallic acid, ethanol, ethoxylated alcohol, DMSO, EDTA, DTPA, other derivative compounds mentioned in this patent, or other commonly used surfactants. Limonene, alone or in combination with other ingredients, may be taken either orally or intravenously or via any other method as to increase the level of limonene alone or with other solvents in the blood thereby temporarily increasing the compounds in the plasma associated with atherosclerosis.

An exemplary diagnostic atherosclerosis assay is set forth below:

A diagnostic solution is intravenously administered over a 2-hour period. The diagnostic solution contains limonene, ethanol, and a surfactant such as ethoxylated alcohol and/or EDTA so as to maintain the following profile: (a) ethanol blood level of about 0.6 ml/l; (b) limonene blood level of about 20 Mm; (c) ethoxylated alcohol blood level of about 4 Mm; and, optionally, (d) EDTA blood level of about 4 Mm. Blood samples are taken hourly for over a 6 hour period and components therein are identified by HPLC & mass spectrometry. The concentration curves of cholesterol (hdl, ldl, vldl), triglycerides, phospholipids, calcium and atherosclerosis debris (compounds or constituents of leukocytes, thrombocytes, and fibrin) are plotted to obtain a plasma profile. This patient specific profile is then compared to a population risk factor statistical data bank. The profile is then correlated to a patients prognosis and recommendations for proper medication, diet and/or invasive procedures may then be made.

The diagnostic test may be minimally invasive, utilizing blood or plasma samples. Alternatively, the sample may comprise a biopsied atherosclerotic plaque sample, such as that taken during a surgical procedure. Sample extracted from a surgical patient are first treated with limonene, then assayed as described in step (c) above.

The diagnostic test is useful not only as a monitor of a patient's potential or predisposition for ischemia or infarction but also as a means for determining the appropriate interventional therapy (e.g., diet, drug therapy, surgery, or a combination thereof) and monitoring the effectiveness thereof or patient compliance therewith.

The plasma profile information obtained may also be used to individualize the therapeutic composition prescribed and administered. The chemical composition of plaque on vascular walls may vary from one individual to another depending on diet, genetics, and other health issues such as smoking, diabetes, etc. It is possible to classify vascular, plaque composition of lipids by size, form and type of oxidation, platelet aggregation (PA), fibrin, leukocytes, calcium and other metals, and bacteria that may initiate plaque formation. After an individual's plaque profile has been obtained, either from plasma sample or plaque biopsy, a combination may be blended pharmaceutically in various proportions such as illustrated in the foregoing examples, to target the individual's need to minimize unwanted vascular adhesion of lipids, PA and other components in the plaque profile for particular individuals and to assist in dissolving existing plaque so that is can be properly metabolized by the body.

Thus, using the information obtained using the diagnostic test described above, one may design an individual therapeutic composition to target the chemical composition of the patient's vascular plaque. Likewise, a check of individual plaque profile from time-to-time via a diagnostic assay may warrant a change in the blend of the components if plaque profile changes occur.

The following examples illustrate aspects of the invention but in no way are intended to limit the scope of the present invention

EXAMPLES

The therapeutic pharmaceutical or nutritional compositions of the present invention may be formulated in a number of ways, using a number of art-accepted and routine techniques. Exemplary compositions and methods of making same are described in Examples 1–8 below. Examples 9–11 describe studies that demonstrate and support the therapeutic utility of the present invention.

EXAMPLE 1

About 250 grams of gallic acid, or a derivative thereof, was dry mixed with about 150 grams of limonene, or a derivative thereof, at about 90° C. The mixture was bathed in nitrogen for about 180 minutes. Next, about 100 grams of ascorbic acid, about 400 grams of lecithin, and about 60 grams of tannic acid were added. The mixture was then placed in an ice bath and cooled.

EXAMPLE 2

About 680 grams of gallic acid, or a derivative thereof, was dry mixed with about 140 grams of limonene, or a derivative thereof, at about 177° C. under reflux conditions, at about 14.9 psi for about 240 minutes in an oxygen deprived atmosphere. The mixture was then cooled while mixing continues. Stabilizers such as those described in Example 1 (i.e., ascorbic acid, lecithin, and tannic acid) were then added.

EXAMPLE 3

About 340 grams of gallic acid, or a derivative thereof, is added to about 140 grams of limonene, or a derivative thereof,. Oxygen is evacuated and the mixture is heated to about 244° C. for about 240 minutes. The temperature is then lowered to about 177° C. Fractional distillation and precipitation is initiated, at Δ25 (i.e., samples are collected at 25° C. increments) at 4 hour intervals to about 295° C. maximum temperature. The balance is cooled and each distillate is refractionalized at least once or as often as necessary. To ensure sample purity, each distillate column is combined with samples eluting at about 75° C. above or below and re-distilled.

EXAMPLE 4

The compositions described in Examples 2 and 3 above and Example 6 below are modified to include varying amounts, about 5 to 100 grains, of one of more of the following antimicrobial agents: sodium hydroxide, bismuth citrate, bismuth permanganate, bismuth difluoroketone, zinc citrate, zinc permanganate, and zinc difluoroketone. The addition of such results in derivatives useful in protecting vascular walls from infectious atherosclerosis.

EXAMPLE 5

By conducting the formulation processes described in Examples 3 and 4 at about 5–16 atmospheres and temperatures corresponding to critical phasing reactions, heterogeneous multimerization is induced.

EXAMPLE 6

Catalysts such as nonmetallic fluoride catalyst, boron trifluoride and phosphorous pentafluoride, are added to the samples of Example 3 (containing about 340 grams of gallic acid, or a derivative thereof, and 140 grams of limonene, or a derivative thereof,) to multimerization reactions. The temperature gradient is inverted (starting at −150° C.) and a non-polar solvent or Lewis acid, if necessary, is added at proper temperatures to induce such reactions. Difluoroketone can also be added to create end products with greater stability and potency.

EXAMPLE 7

Appropriate compounds are added to the compositions described in Examples 3 and 6 to create the derivatives shown below:

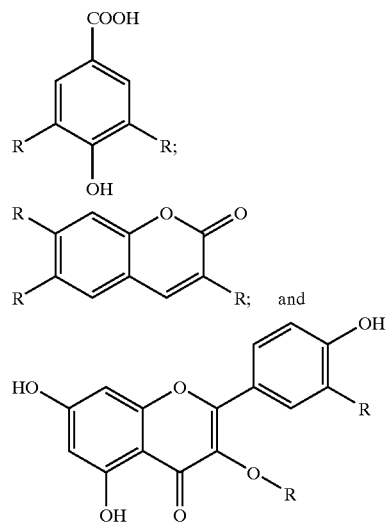

wherein R is hydrogen, halogen, guano, amino, nitro, cyano or acetate. These derivatives are particularly useful in increasing vasodilatation, inhibiting plaque accumulation and preventing thrombotic occlusion. Unlike aspirin, the therapeutic benefit ascribed to administration of the derivatives described in this Example is not adversely affected by adrenaline.

EXAMPLE 8

About 340 grams of gallic acid, or a derivative thereof, is added to about 70 grams of limonene, or a derivative thereof, and about 200 grams of glucose in about 800 ml of water. Varying amounts of additive compounds such as those described in the above Examples (i.e., ascorbic acid, lecithin, tannic acid, sodium hydroxide, bismuth citrate, bismuth permanganate, bismuth difluoroketone, zinc citrate, zinc permanganate, and zinc difluoroketone) may also be added. About 4 grams of ethoxylated alcohol may be added if needed. The mixture is then aerated with up to 8 grams of $O_2$ in an otherwise oxygen deprived vessel at 100° C. under reflux for up to 280 minutes. The temperature may be raised up to as much as 150° C. under reflux over 90 minutes, then cooled gradually. Fractional distillation and precipitation is started at Δ25 (see above) and a vacuum up to 10 psi is created to aid in chemical separation. Appropriate distillate columns are selected and used. Precipitated compounds are then purified. The compositions may be particularly adjusted to correspond to a particular atherosclerosis profile so as to minimize accumulation on and maximize removal of atherosclerosis from vascular walls.

EXAMPLE 9

To compare the effects of prior art compositions alone to those of the present invention, a 12 week rabbit study was conduced. Eight rabbits were fed a diet containing 0.01% polyphenols while eight others were fed a diet containing 0.01% polyphenols and perillyl alcohol, a metabolite of d-limonene. The latter group showed an over 20% decrease of atherosclerosis.

EXAMPLE 10

To study the effects of limonene on the solubility of cholesterol, 10 test tubes were coated with cholesterol. Five were then filled with an aliquot of plasma sample extracted from healthy adult volunteer. The remaining five were filled with a human plasma sample containing limonene at a concentration of 10 micrograms per ml. The test tubes were stirred for one hour. The concentration of cholesterol in solution for each tube was then assayed. Those samples treated with limonene demonstrated a 24% increase in the rate of cholesterol solubility.

EXAMPLE 11

To demonstrate the beneficial effects of the excipient, lecithin, five healthy adult male volunteers were given 12 ml of d-limonene alone and then 12 ml of d-limonene with 16 grams of bread. All experienced moderate gastrointestinal (GI) discomfort. The same volunteers were then given 12 ml of d-limonene with 4 grams of lecithin. Only one volunteer experienced mild discomfort while the remaining 4 experienced no GI discomfort at all.

Chemical compounds described herein can be further purified via numerous art-accepted methods such as silica thin layer chromatography using hexane/ethyl acetate (8:2) as solvent system, dissolved in a halo-carbon solvent and t-butyl hydroperoxide (1:4). Likewise the compounds can be conveniently separated by either column chromatography or thin layer chromatography or high pressure chromatography. Also, some compounds can be economically separated by $CO_2$ critical phase extraction.

The disclosure of each publication, patent or patent application mentioned in this specification is specifically incorporated by reference herein in its entirety.

The invention has been illustrated by reference to specific examples and preferred embodiments. It should be understood that the invention is intended not to be limited by the foregoing description, but to be defined by the appended claims and their equivalents.

What is claimed is:

1. A method for treating stenotic vascular disorders in animals comprising administering a composition comprising (i) a therapeutically effective amount of limonene or a derivative thereof and (ii) a therapeutically effective amount of a multimer of gallic acid.

2. The method according to claim 1, wherein said composition comprises about 35 wt. % to about 70 wt. % garlic acid multimer and about 5 wt. % to about 55 wt. % limonene or a derivative thereof.

3. The method according to claim 1, wherein said composition further comprises an effective amount of an antioxidant stabilizing agent.

4. The method according to claim 3, wherein said antioxidant stabilizing agent is selected from the group consisting of ascorbic acid, tocopherol, lecithin, tannic acid and salts thereof.

5. The method according to claim 4, wherein said antioxidant stabilizing agent is lecithin.

6. The method according to claim 3, wherein said antioxidant stabilizing agent comprises about 10 wt. % to about 60 wt. % of said composition.

7. The method according to claim 1, wherein said composition further comprises an antimicrobial agent selected from the group consisting of sodium hydroxide, bismuth citrate, bismuth permanganate, bismuth difluoroketone, zinc citrate, zinc permanganate, and zinc difluoroketone.

8. The method according to claim 1, wherein said gallic acid multimer comprises gallic acid lignin attached to either glucose or limonene.

9. The method according to claim 1, wherein said composition comprises a derivative of limonene, said derivative being selected from the group consisting of oxidation products, salts, solvates, multimers, prodrugs and metabolites thereof.

10. The method according to claim 9, wherein said limonene derivative is selected from the group consisting of perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

11. The method according to claim 1, further comprising the co-administration of aspirin with said composition.

12. The method according to claim 1, further comprising the co-administration of a cholesterol lowering agent with said composition.

13. The method according to claim 1, wherein said gallic acid multimer comprises repeating monomers of gallic acid or a derivative thereof linked via nitrogen containing linking moities.

14. A composition comprising (i) a therapeutically effective amount of limonene or a derivative thereof, and (ii) a therapeutically effective amount of a multimer of gallic acid.

15. The composition according to claim 14, wherein said composition comprises about 35 wt. % to about 70 wt. % gallic acid multimer and about 5 wt. % to about 55 wt. % limonene or a derivative thereof.

16. The composition according to claim 14, wherein said composition further comprises an effective amount of an antioxidant stabilizing agent.

17. The composition according to claim 16, wherein said antioxidant stabilizing agent is selected from the group consisting of ascorbic acid, lecithin, tocopherol, tannic acid and salts thereof.

18. The composition according to claim 16, wherein said antioxidant stabilizing agent is lecithin.

19. The composition according to claim 16, wherein said antioxidant stabilizing agent comprises about 10 wt. % to about 60 wt. % of said composition.

20. The composition according to claim 14, wherein said gallic acid multimer comprises gallic acid lignin attached to either glucose or limonene.

21. The composition according to claim 14, wherein said composition comprises a derivative of limonene, said derivative being selected from the group consisting of oxidation products, salts, solvates, multimers, prodrugs and metabolites thereof.

22. The composition according to claim 21, wherein said limonene derivative is selected from the group consisting of perillyl alcohol, perillic acid, cis-dihydroperillic acid, trans-dihydroperillic acid, methyl esters of perillic acid, methyl esters of dihydroperillic acid, limonene-2-diol, uroterpenol and combinations thereof.

23. The composition according to claim 14, wherein said composition further comprises an antimicrobial agent selected from the group consisting of sodium hydroxide, bismuth citrate, bismuth permanganate, bismuth difluoroketone, zinc citrate, zinc permanganate, and zinc difluoroketone.

24. The composition according to claim 14, wherein said gallic acid multimer comprises repeating monomers of gallic acid or a derivative thereof linked via nitrogen containing linking moities.

* * * * *